United States Patent
Miller

(10) Patent No.: US 9,839,504 B2
(45) Date of Patent: Dec. 12, 2017

(54) IMPLANTABLE SLINGS

(71) Applicant: Covidien LP, Mansfield, MA (US)

(72) Inventor: Jeffrey Miller, East Haven, CT (US)

(73) Assignee: Covidien LP, Mansfield, MA (US)

( * ) Notice: Subject to any disclaimer, the term of this patent is extended or adjusted under 35 U.S.C. 154(b) by 170 days.

(21) Appl. No.: 14/280,759

(22) Filed: May 19, 2014

(65) Prior Publication Data

US 2014/0371521 A1    Dec. 18, 2014

Related U.S. Application Data

(60) Provisional application No. 61/836,364, filed on Jun. 18, 2013.

(51) Int. Cl.
*A61F 2/00* (2006.01)

(52) U.S. Cl.
CPC .......... *A61F 2/0063* (2013.01); *A61F 2/0045* (2013.01); *A61F 2210/0004* (2013.01); *A61F 2220/0016* (2013.01)

(58) Field of Classification Search
CPC .................. A61F 2/0063; A61F 2/0045; A61F 2220/0016; A61F 2210/0004
See application file for complete search history.

(56) References Cited

U.S. PATENT DOCUMENTS

| | | |
|---|---|---|
| 3,320,649 A | 5/1967 | Naimer |
| 3,718,725 A | 2/1973 | Hamano |
| 4,338,800 A | 7/1982 | Matsuda |
| 4,391,106 A | 7/1983 | Schafer et al. |
| 4,476,697 A | 10/1984 | Schafer et al. |
| 4,709,562 A | 12/1987 | Matsuda |
| 5,254,127 A | 10/1993 | Wholey et al. |
| 5,254,133 A | 10/1993 | Seid |
| 5,330,445 A | 7/1994 | Haaga |
| 5,356,432 A | 10/1994 | Rutkow et al. |
| 5,569,273 A | 10/1996 | Titone et al. |
| 5,761,775 A | 6/1998 | Legome et al. |
| 5,906,617 A | 5/1999 | Meislin |

(Continued)

FOREIGN PATENT DOCUMENTS

| | | |
|---|---|---|
| DE | 19832634 A1 | 1/2000 |
| EP | 0276890 A2 | 8/1988 |

(Continued)

OTHER PUBLICATIONS

European Search Report, Application No. 14 17 2688 dated Sep. 26, 2014.

(Continued)

*Primary Examiner* — Christine H Matthews
*Assistant Examiner* — Joshua D Lannu

(57) ABSTRACT

The present disclosure describes implantable slings suitable for use in a variety of medical applications, the implantable slings include at least one a biocompatible support member having a first surface and a second surface, the first and second surfaces including a first end, a second end, and a central region positioned therebetween, a first set of fixation elements positioned on the first end of the first surface, a second set of fixation elements positioned on the second end of the first surface, and a spacer positioned on the central region of the first surface for contacting a tissue in need of support.

21 Claims, 11 Drawing Sheets

(56) References Cited

U.S. PATENT DOCUMENTS

| | | | |
|---|---|---|---|
| 6,039,741 A | 3/2000 | Meislin | |
| 6,110,210 A | 8/2000 | Norton et al. | |
| 6,120,539 A | 9/2000 | Eldridge et al. | |
| 6,408,656 B1 | 6/2002 | Ory et al. | |
| 6,443,964 B1 | 9/2002 | Ory et al. | |
| 6,596,002 B2 | 7/2003 | Therin et al. | |
| 6,638,284 B1 | 10/2003 | Rousseau et al. | |
| 6,971,252 B2 | 12/2005 | Therin et al. | |
| 6,991,643 B2 | 1/2006 | Saadat | |
| 7,083,637 B1* | 8/2006 | Tannhauser | A61B 1/00087 606/222 |
| 7,213,421 B2 | 5/2007 | Shirasaki et al. | |
| 7,331,199 B2 | 2/2008 | Ory et al. | |
| 7,614,258 B2 | 11/2009 | Cherok et al. | |
| 2004/0039453 A1* | 2/2004 | Anderson | A61B 17/0401 623/23.72 |
| 2004/0073235 A1* | 4/2004 | Lund | A61B 17/1227 606/151 |
| 2004/0225181 A1* | 11/2004 | Chu | A61B 17/06109 600/37 |
| 2006/0281967 A1 | 12/2006 | Meneghin et al. | |
| 2007/0032695 A1* | 2/2007 | Weiser | A61B 17/06109 600/29 |
| 2007/0038018 A1* | 2/2007 | Chu | A61F 2/0045 600/37 |
| 2007/0043255 A1* | 2/2007 | O'Donnell | A61F 2/0045 600/30 |
| 2008/0081945 A1* | 4/2008 | Toso | A61F 2/0045 600/37 |
| 2008/0161837 A1* | 7/2008 | Toso | A61F 2/0045 606/151 |
| 2008/0195231 A1 | 8/2008 | Ory et al. | |
| 2008/0208360 A1 | 8/2008 | Meneghin et al. | |
| 2008/0269548 A1 | 10/2008 | Vecchiotti et al. | |
| 2009/0036907 A1 | 2/2009 | Bayon et al. | |
| 2010/0049222 A1 | 2/2010 | Cherok et al. | |
| 2010/0312043 A1* | 12/2010 | Goddard | A61F 2/0045 600/30 |
| 2011/0230707 A1* | 9/2011 | Roll | A61F 2/0045 600/37 |

FOREIGN PATENT DOCUMENTS

| | | |
|---|---|---|
| EP | 0719527 A1 | 7/1996 |
| EP | 0797962 A2 | 10/1997 |
| EP | 827724 A2 | 3/1998 |
| EP | 0836838 A1 | 4/1998 |
| FR | 2744906 A1 | 8/1997 |
| FR | 2766698 A1 | 2/1999 |
| FR | 2779937 A1 | 12/1999 |
| WO | 9507666 A1 | 3/1995 |
| WO | 9603091 A1 | 2/1996 |
| WO | 96/41588 A1 | 12/1996 |
| WO | 03092546 A2 | 11/2003 |
| WO | 03105727 A1 | 12/2003 |
| WO | 2013020076 A1 | 2/2013 |

OTHER PUBLICATIONS

European Office Action dated Aug. 29, 2016 in corresponding European Patent Application No. 14172688.5, 5 pages.
European Office Action dated Jan. 20, 2017 in corresponding European Patent Application No. 14172688.5, 5 pages.

* cited by examiner

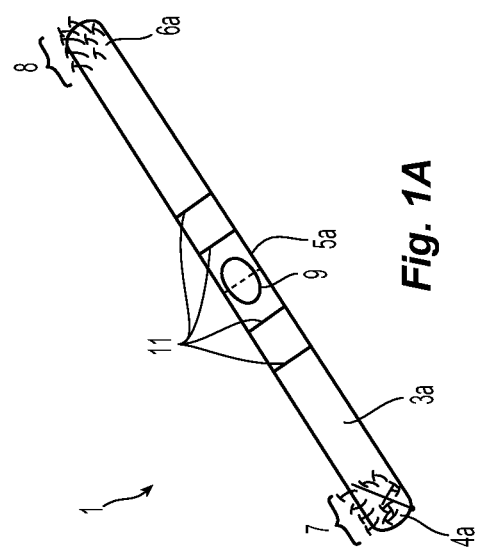
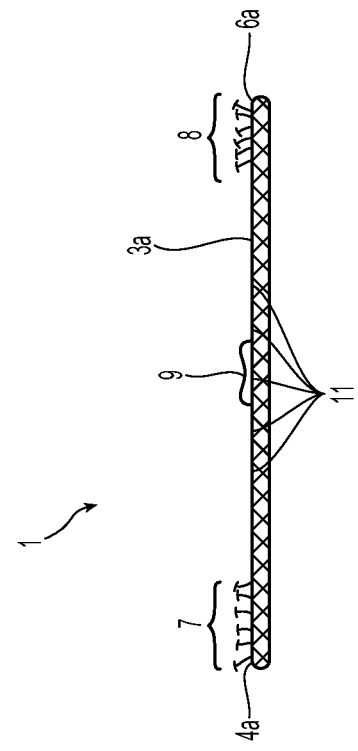
Fig. 1A
Fig. 1B

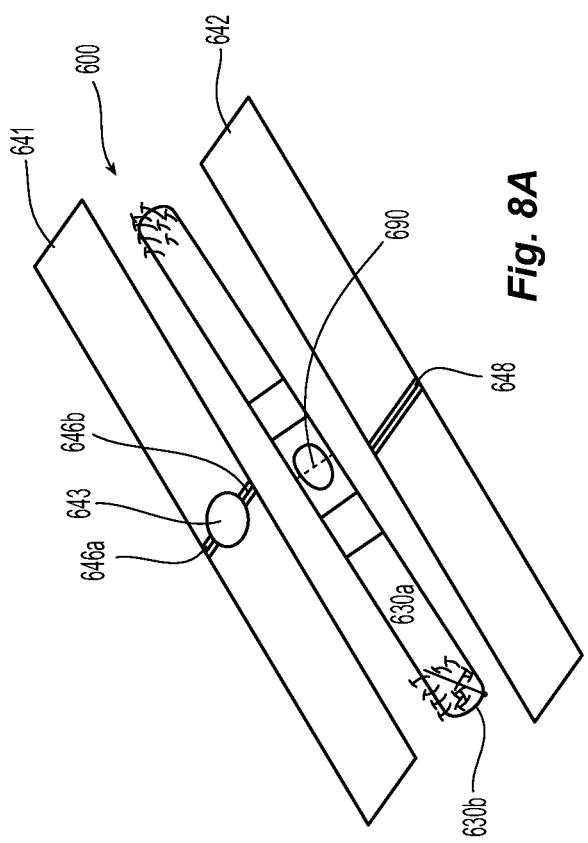
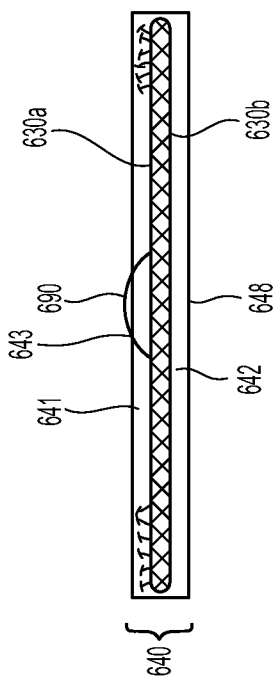
Fig. 8A
Fig. 8B

IMPLANTABLE SLINGS

CROSS-REFERENCE TO RELATED APPLICATIONS

This application claims the benefit of and priority to U.S. Provisional Patent Application No. 61/836,364, filed Jun. 18, 2013, the entire disclosure of which is incorporated by reference herein.

BACKGROUND

1. Technical Field

The present disclosure relates to implantable surgical slings, and particularly, implantable surgical slings which include a support member, a plurality of tissue fixation elements, and a spacer, having application in supporting tissue inside the body and particularly, for treating stress urinary incontinence.

2. Description of Related Art

Stress urinary incontinence (SUI) is a female medical condition commonly associated with weakening of the pelvic muscles and/or connective tissues that support the urethra in its proper position. As a result of this condition, involuntary urine leakage occurs from simple physical activity, such as running or jumping, and even coughing or sneezing, as the urethra is not properly supported and does not remain fully closed during such activity.

An increasingly widespread technique for treating stress urinary incontinence is that of sling suspension. Generally, sling suspension procedures involve the placement of a sling beneath the patient's urethra and securing the sling to tissue located inside the pelvis region, including hard or soft tissue, such as bone, muscle, and/or fascia. In some procedures the sling passes through a patient's skin and may be anchored outside the body. An introducer may be used to help properly position the sling.

A traditional sling procedure may involve placing a strip of an implant material (e.g., natural tissue or synthetic mesh) under a tissue in need of support, i.e., urethra, and securing the strip to the surrounding tissue. In many instances, separate surgical fasteners, such as sutures, staples, cables, screws, pins, and the like, may be used to attach the sling to the tissue. In such instances, the surgical fastener must penetrate the tissue to a sufficient depth, i.e., in a non-superficial manner, to properly secure and/or anchor the sling into position, thereby inflicting trauma to the surrounding tissue.

It would be beneficial to provide an implantable sling which can attach directly to the tissue, with or without the use of a surgical fastener, wherein attachment is superficial and does inflict additional trauma to the tissue.

SUMMARY OF THE INVENTION

The present disclosure describes implantable slings suitable for use in a variety of medical applications, the implantable slings include at least one a biocompatible support member having a first surface and a second surface, the first and second surfaces including a first end, a second end, and a central region positioned therebetween, a first set of fixation elements positioned on the first end of the first surface, a second set of fixation elements positioned on the second end of the first surface, and a spacer positioned on the central region of the first surface for contacting a tissue in need of support.

The implantable sling may further include at least one additional set of fixation elements. The additional sets of fixation elements may be positioned on the second surface of the support member. In embodiments, the additional sets of fixation elements may be positioned on the first and second ends of the support member. In embodiments, the additional sets of fixation elements may be positioned between both ends of the support member and the central region of the support member. In embodiments, a single set of additional fixation elements may be positioned on the central region of the second surface of the support member.

The implantable sling may further include at least one additional spacer. The additional spacer may be positioned on the second surface of the support member. In embodiments, at least two additional spacers may be positioned on the first and second ends of the second surface of the support member. In embodiments, the additional spacer may be positioned between both ends of the support member and the central region of the support member. In embodiments, a single spacer may be positioned on the central region of the second surface of the support member.

In embodiments, the spacer may be made from a fast-resorbing material.

In embodiments, the support member may be a knitted mesh.

In embodiments, the implantable slings described herein further include an outer protective sheath. In embodiments, the outer sheath includes at least one cut-out which allows the spacer to protrude from the cut-out prior to removal of the sheath.

Methods of treating urinary incontinence are also disclosed. In embodiments, a method of treating urinary stress incontinence includes: obtaining an implantable sling comprising a biocompatible support member having a first surface and a second surface, the first and second surfaces including a first end, a second end, and a central region positioned therebetween, a first set of fixation elements positioned on the first end of the first surface, a second set of fixation elements positioned on the second end of the first surface; and, a spacer positioned on the central region of the first surface; positioning the spacer beneath an urethra; attaching the first set of fixation elements to an obturator internus muscle on a first lateral side of the urethra and the second set of fixation elements to the obturator internus muscle on a second lateral side of the urethra. In embodiments, at least one end of the implantable slings can be folded and/or rolled to shorten the length of the sling without trimming.

These and other objects, features and advantages will be apparent from the following detailed description of illustrative embodiments thereof, which is to be read in connection with the accompanying drawings.

BRIEF DESCRIPTION OF THE DRAWINGS

FIG. 1A is a perspective view of a surgical sling in accordance with at least one embodiment described herein.

FIG. 1B is a side view of the surgical sling depicted in FIG. 1A.

FIGS. 8A and 8B are a perspective view and a side view of a surgical sling described herein and shown with one example of an outer protective sheath.

DETAILED DESCRIPTION

Figure 2A:
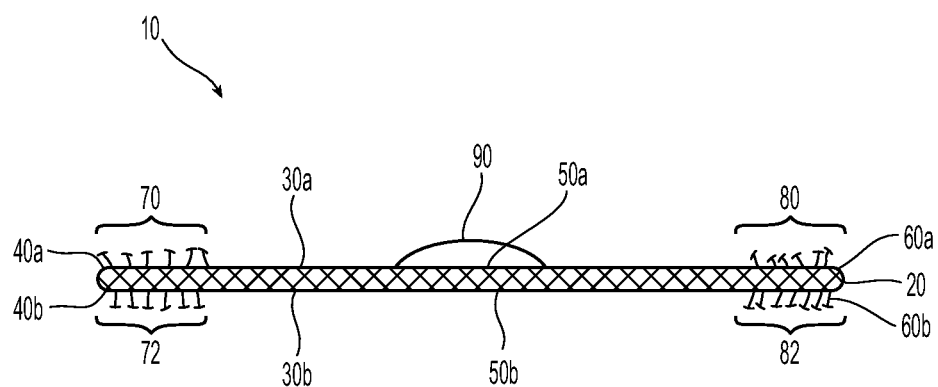
FIGS. 2A-2B are each a side view of a surgical sling in accordance with at least one embodiment described herein.

Although the present invention is described in detail in relation to its use as a sub-urethral implantable sling for treating stress urinary incontinence, it is to be understood that the present disclosure is not so limited, as there are numerous other applications suitable for such an implant. For example, the implantable slings described herein could be used for repairing pelvic floor defects such as, but not limited to, cystoceles, enteroceles, and rectoceles, and for hernia repair or other prolapse conditions, or for supporting or otherwise restoring other types of tissue.

Turning initially to FIGS. 1A-1B, one embodiment of an implantable sling 1 in the form of a sub-urethral sling particularly suited for the treatment of stress urinary incontinence (SUI) includes an implantable, elongated support member 2. The support member 2 has a multiplicity of openings formed through the thickness thereof, and includes a first surface 3a and a second surface 3b, each surface including a first end 4a, 4b a second end 6a, 6b longitudinally opposite the first end 6a, 6b and a central region 5a, 5b positioned therebetween.

As further illustrated, the implantable sling 1 includes a first set of fixation elements 7 positioned on the first end 4a of the first surface 3a, a second set of fixation elements 8 positioned on the second end 6a of the first surface 3a, and a spacer 9 positioned on the central region 5a of the first surface 3a. Additional markings 11 are depicted to assist a surgeon with properly positioning the implantable sling 1 during implantation and/or measuring the distance between the tissue in need of support, e.g., the urethra, and the tissue which the ends are suspended from.

The implantable slings include at least a support member, a first and second set of fixation elements and a spacer. Any biocompatible material may be used to form the support member, fixation elements and/or spacer described herein. For example, the support member may be made from natural, synthetic, bioabsorbable or non-bioabsorbable materials. It should of course be understood that any combination of natural, synthetic, bioabsorbable and non-bioabsorbable materials may be used to form the support members, fixation elements or spacer described herein.

The term "bioabsorbable" as used herein is defined to include both biodegradable and bioresorbable materials. By bioabsorbable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Representative natural bioabsorbable materials include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic bioabsorbable polymers include polyhydroxy acids prepared from lactone monomers, such as glycolide, lactide, caprolactone, $\epsilon$-caprolactone, valerolactone, and $\delta$-valerolactone, as well as pluronics, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly (hydroxyvaleric acid); poly(lactide-co-($\epsilon$-caprolactone-)); poly(glycolide-co-($\epsilon$-caprolactone)); polycarbonates; poly (pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof. In certain embodiments, the biocompatible support member(s), fixation elements(s) and/or spacer(s) may be formed using a combination of bioabsorbable and non-bioabsorbable polymers.

Some non-limiting examples of suitable non-bioabsorbable materials include polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, including expanded polytetrafluoroethylene (ePTFE) and condensed polytetrafluoroethylene c(PTFE), fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

Some examples of suitable biocompatible support members include foams, meshes, tapes, and the like. In some embodiments, the biocompatible support member is a surgical mesh. In some embodiments, the biocompatible support member is planar. In some embodiments, the support member is a multi-armed surgical mesh.

The biocompatible support members may be formed using any method within the purview of those skilled in the art. Some non-limiting examples include, weaving, knitting, braiding, crocheting, extruding, spraying, casting, molding, and combinations thereof. In some embodiments, the biocompatible support member may be a two or three dimensional surgical mesh which is woven, knitted, braided, or crocheted from at least one first filament to form the support member. The at least one filament may be a monofilament or a multifilament. In certain embodiments, the biocompatible support member may be a surgical mesh consisting of at least one first filament made of polyethylene terephthalate.

The sling, including the support member, the fixation elements and the spacer will be suitably dimensioned in accordance with its application(s) as described. For example, one embodiment described in detail below that is particularly suitable for treatment of stress urinary incontinence in women includes a sling having a width of approximately 2-30 millimeters, in embodiments 15-25 millimeters, and having a length between about 50-300 millimeters, in embodiments about 100-250 millimeters. In particularly embodiments, the sling may be about 20 millimeters wide and about 200 millimeters long.

It is envisioned that the slings described herein may be of any shape including elliptical, square, triangular, hexagonal, rectangular and circular. However, in particularly useful embodiments, the slings described herein may display a length greater than its width and may or may not include rounded corners.

The fixation elements described herein, which are positioned on at least a portion of the biocompatible support member, may be formed from the same first filament used to form the support member and/or may be formed using a different second filament. The second filament may be a monofilament or multifilament. The second filament may be made from any biocompatible, bioabsorbable, or non-bioabsorbable material, including those described herein. In some embodiments, the first and second filaments may be made from the same materials. In other embodiments, the first and second filaments may be made from different materials. For example, in some embodiments, the biocompatible support member may be formed from at least one first filament made from a non-bioabsorbable material, e.g., polypropylene, polyethylene terephthalate, polytetrafluoroethylene, etc., and the fixation elements may be formed from at least one second filament made from a bioabsorbable material, i.e., polylactic acid, polyglycolic acid, and the like. In yet another example, the biocompatible support member may be formed from at least one first filament made from a bioabsorbable material and the fixation elements may be formed from at least one second filament made from a non-bioabsorbable material.

The fixation elements may include any configuration of filaments which extend from a surface of the support member in a manner which attaches and/or adheres the substrate to tissue. In embodiments, the fixation elements possess the ability to attach the support member to the tissue without significantly penetrating and/or perforating the tissue. In some embodiments, the fixation elements attach the sling directly to the tissue, wherein attachment is superficial and does inflict additional trauma to the tissue.

Some non-limiting examples of fixation element configurations include loops, hooks, spiked naps, barbed loops, barbed hooks, barbed spiked naps and combinations thereof. The fixation elements may be disposed in various arrangements along a surface of the support member. The fixation elements may be formed using any suitable method, including but not limited to, injection molding, stamping, cutting, laser, ultrasonics, melting, and combinations thereof. In embodiments wherein the fixation elements include barbs, the barbs may be uni-directional, multi-directional, symmetrical, non-symmetrical, and combinations thereof.

The second filaments used to form the fixation elements may be barbed at any time during the manufacturing of the implants described herein. In some embodiments, the second filaments may be barbed prior to being incorporated into the biocompatible support member. In some embodiments, the second filaments may be barbed after being incorporated into the biocompatible support member. In still other embodiments the second filaments may be barbed while being incorporated into the biocompatible support member.

In certain embodiments, the fixation elements may be made form second filaments added to the support member as loops which extend from at least one surface of a biocompatible support member in a generally perpendicular manner. In other embodiments, the fixation elements may be made from a plurality of second filaments which individually extend from the surface of a biocompatible support member in a generally perpendicular manner.

By generally perpendicular, the fixation elements may protrude from the surface of the support member at about 90 degrees. In embodiments, the fixation elements may protrude from the surface of the support member from about 45 to about 135 degrees, and in embodiments from about 60 to about 120 degrees. In still other embodiments, the support members may include fixation elements which extend from a combination of surfaces and/or directions of the implantable sling.

In embodiments, the fixation elements may be filaments knitted in combination with filaments of the support member to form a knitted mesh and having the fixation elements and the fibers of the support member intertwined to form the sling. In embodiments, the filaments forming the fixation elements and the filaments forming the support member may be interconnected in a manner which can not be separated.

Figure 12:
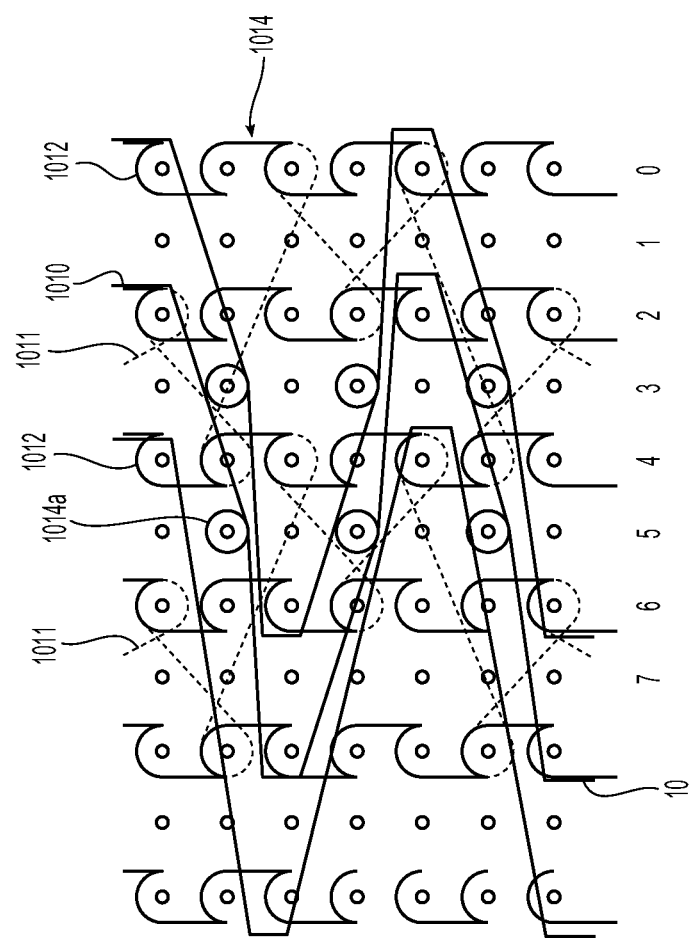
FIG. 12 is a diagram showing a weave pattern for forming the portion of the implantable slings described herein which include at least one set of fixation elements in accordance with at least one embodiment described herein.

In certain embodiments, the implantable medical device may be a surgical mesh which is made from a plurality of first and second filaments knitted in any suitable manner that allows the filaments to form a support member and form loops or naps along different portions of the sling. The loops or naps extend from at least one surface of the support member. FIG. 12 diagrams one representative pattern that will form fixation elements along portions of the support member in accordance with the present disclosure. The implantable sling may be made on a warp knitting machine, of the tricot or Raschel type, with at least three sheets or warps of yarn and as many guide bars.

The front and intermediate guide-bars may be threaded with a first set of filaments or yarns. The intermediate bars may be threaded, one guide full, three guides empty, with monofilament or multifilament yarn. This yarn may be made from any suitable biocompatible material; and in some embodiments, may be made from polyethylene terephthalate. This filament or yarn is represented by a broken line and by reference number 1011 in FIG. 12. The intermediate bar works in such a way as to obtain a zigzag openwork pattern between the columns of meshes.

The front bar is threaded; one guide full, one guide empty, and works in chain weave with a multifilament or monofilament yarn, represented by number 1012 in FIG. 12. The chain stitch imprisons the monofilament 1010 and maintains the knit in length while contributing to the formation of the knit with the intermediate sheet formed by yarn 1011.

The rear bar may be threaded, one guide full and one guide empty, with a second filament, i.e., monofilament or multifilament. This second filament or yarn may be made from any suitable biocompatible material; and in some embodiments, may be made from polylactic acid.

The diameter of the second filament is over 0.10 millimeter. In practice, this diameter is between 0.14 and 0.18 millimeter and is of the order of 0.15 millimeter. This yarn or filament is represented by reference number 1010 and in a solid line in FIG. 12.

The different filaments may be worked according to the following chart:

| Warp | | |
|---|---|---|
| Rear bar I | Intermediate bar II Raschel | Front bar III |
| Front bar II | Intermediate bar II | Rear bar III |
| 7 | 3 | 1 |
| 7 | 2 | 0 |
| — | — | — |
| 3 | 4 | 0 |
| 4 | 5 | 1 |
| — | — | — |
| 0 | 1 | |
| 0 | 0 | |
| — | — | |
| 4 | 2 | |
| 3 | 3 | |
| | — | |
| | 1 | |
| | 0 | |
| | — | |
| | 4 | |
| | 5 | |

The rear bar places the yarn in partial weft under the chain stitch and "thrown" onto the needle not forming a chain stitch. For this reason, at the next row, the needle not forming a chain stitch not being supplied permits escape of the monofilament mesh which forms a loop (see FIG. 13) projecting from at least one surface of the sling.

The sling thus obtained may be a knit provided with loops along portions of the knit as described herein and which are generally perpendicular to one of the surfaces of the support member. The loops also display the rigidity to hold at about a right angle, which is obtained by the rigidity or nerve of the second filament employed. This rigidity or nerve may be necessary for the subsequent formation of the spiked naps, barbed spiked naps, hooks, barbed hooks, and/or barbed loops which ensure a tissue-gripping and/or tissue-attaching function.

Other patterns by which to obtain a knit with fixation elements that protrude from at least one surface should be apparent to one skilled in the art. For example, the knit described herein may be stitched with loops on at least two surfaces of the mesh. In addition, the portions of the support member which do not include fixation elements may be formed using any suitable knitting pattern.

Figure 13:
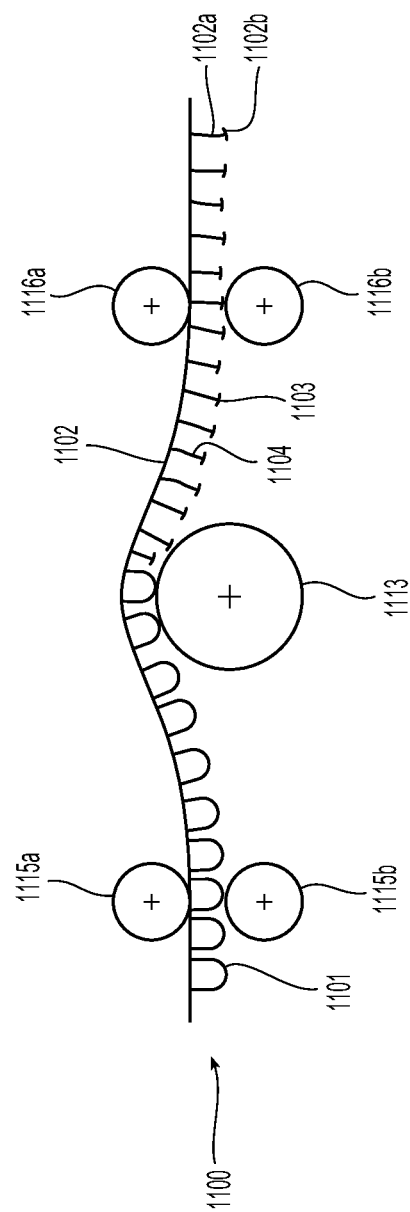
FIG. 13 is a diagrammatic side view of a device permitting the formation of the fixation elements on at least one surface of the implantable slings described herein in accordance with at least one embodiment described herein.

FIG. 13 illustrates one method by which the fixation elements can be converted from the loops 1101 into the spiked and naps 1102. In one embodiment, the method includes passing the support member 1100 with the loops 1101 over the cylinder 1113 containing an electrical heating resistor. Support member 1100 may be pressed flat on cylinder 1113 by two pairs of rollers, upstream 1115*a*, 1115*b* and downstream 1116*a*, 1116*b*, respectively, which may be vertically displaceable for controlling and/or alternating the pressing force dependent upon the varying thickness of different portions of the sling. This control as well as that of the temperature of the resistor placed in cylinder 1113 and of the speed of movement of substrate 1100 across cylinder 1113 make it possible to melt the head of each of the loops 1101 so that each loop 1101 forms two spiked naps 1102.

Each spiked nap 1102 thus has a substantially rectilinear body 1104 protruding perpendicularly with respect to the substrate 1100. Rectilinear body 1104 includes attached end 1102*a* and free end 1102*b*, with free end 1102*b* having spike 1103 of greater width than that of the body 1104. Spike 1103 may have the shape of a sphere or mushroom.

In addition to the fixation elements, the support members described herein also include at least one spacer. In embodiments, the spacer is centrally located along the elongate support member. The spacer is intended to be positioned beneath the tissue in need of support, i.e., the urethra, and initially separate the tissue from attaching directly to the sling. The spacer may be useful in centering the sling beneath the tissue. The spacer is intended to provide the ideal spacing between the sling and the tissue. In embodiments, the spacer obviates the need for a dilator, clamp and/or other mechanism employed by surgeons to set the distance between the sling and the tissue in need of support.

In embodiments, the spacer may be a flat film positioned on the surface of the support member. In embodiments, the spacer may be a rounded bleb of material. In embodiments, the spacer may have a thickness greater than the thickness of support member. In some embodiments, the top surface of the spacer may be contoured to mirror the outer surface of the tissue intended to be supported. For example, in the case of the urethra, which is tubular, the top surface of the support member may include a concave surface to allow the tubular urethra to properly sit inside the spacer.

In embodiments, the spacer may be made from a fast resorbing material which resorbs and/or dissolves within a few hours of implantation. In embodiments, the fast resorbing material may be resorbed and/or dissolved within an hour of implantation. Exemplary, non-limiting, fast resorbing and/or dissolvable materials from which the spacer may be made include, but are not limited to, alginates, sugar based formulations, starches, collagen, chitosans, dextrans, gelatins, cellulose, polyvinyl alcohol, polyglycolic acid (PGA), polylactic acid (PLA), polydioxanone (PDO), and/or other synthetic or natural polymers including combinations thereof.

In embodiments, the slings described herein may include additional spacers. In some embodiments, the additional spacers may be positioned on the first or second end of the support member.

In embodiments, the support member, fixation elements and/or spacer of the implantable slings described herein can be combined with and/or coated with a bioactive agent. The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent that provides a therapeutic or prophylactic effect, a compound that effects or participates in tissue growth, cell growth, cell differentiation, and an anti-adhesive compound, a compound that may be able to invoke a biological action such as an immune response, or could play any other role in one or more biological processes. It is envisioned that the bioactive agent may be applied to any portion of the sling in any suitable form, e.g., films, powders, liquids, gels, foams, and the like.

Figure 2B:
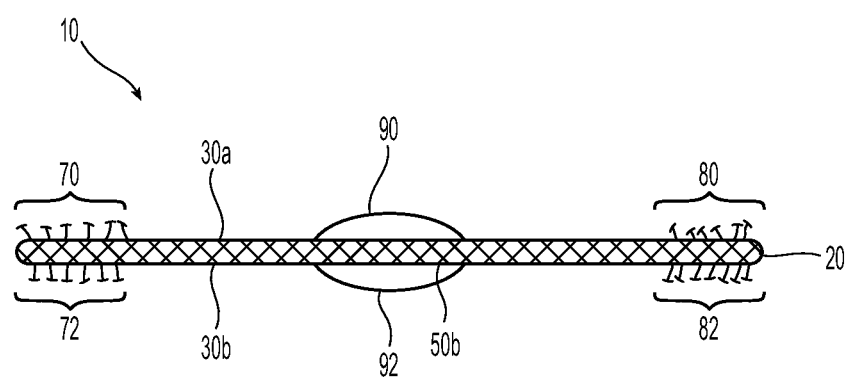

Returning again to the drawings, FIGS. 2A-2B depicts an implantable sling 10 which includes an implantable, elongated support member 20. The support member 20 has a multiplicity of openings formed through the thickness thereof, and includes a first surface 30a and a second surface 30b, each surface including a first end 40a, 40b a second end 60a, 60b longitudinally opposite the first end 40a, 40b, and a central region 50a, 50b positioned therebetween.

As further illustrated, the implantable sling 10 includes a first set of fixation elements 70 positioned on the first end 40a of the first surface 30a, a second set of fixation elements 80 positioned on the second end 60a of the first surface 30a, and a spacer 90 positioned on the central region 50a of the first surface 30a. In addition, a third set of fixation elements 72 are positioned on the first end 40b of the second surface 30b and a fourth set of fixation elements 82 are positioned on the second end 60b of the second surface 30b.

In some embodiments, as depicted in FIG. 2B, the implantable sling 10 further includes a second spacer 92 positioned on the central region 50b of the second surface 30b.

Figure 3A:
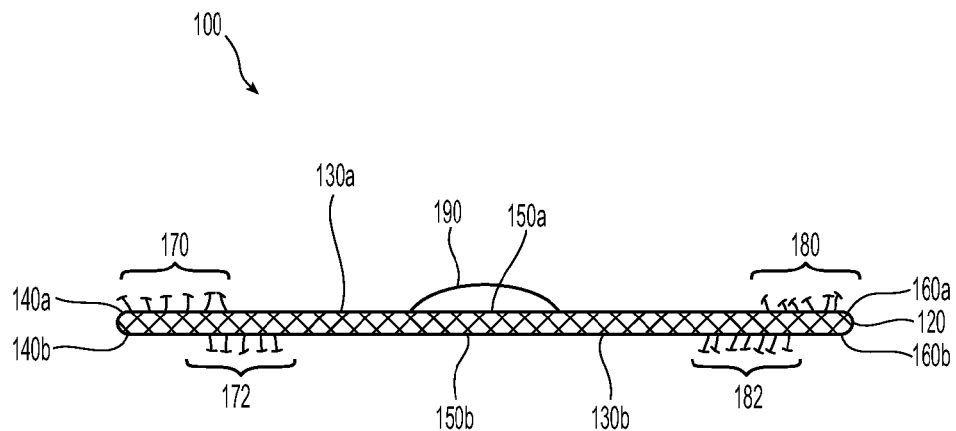
FIGS. 3A-3C are each a side view of a surgical sling in accordance with at least one embodiment described herein.
Figure 3B:
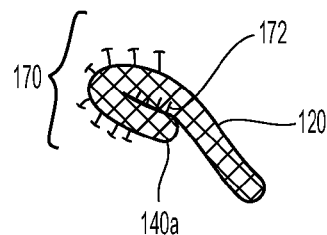

As illustrated in FIGS. 3A-3B, the implantable sling 100 may include support member 120 including first surface 130a and a second surface 130b. The first surface 130a containing a first end 140a having a first set of fixation elements 170, a second end 160a having a second set of fixation elements 180, and a central region 150a including a first spacer 190. The second surface 130b containing a third set of fixation elements 172 positioned between the first end 140b and the central region 150b. The second surface 130b also containing a fourth set of fixation elements 182 positioned between the second end 160b and the central region 150b. As illustrated, in some embodiments, the third and/or fourth set of fixation elements 172, 182, can be positioned opposite and off-set the first and second set of fixation elements.

By spacing the third and fourth set of fixation elements away from the ends of the support member, the first and second ends may be more easily folded and/or rolled over to shorten the length of the sling, if needed. In such instances, at least a portion of the third and fourth fixation elements may be used to lock the folded and/or rolled portion of the support member into position. As illustrated in FIG. 3B, first end 140a is folded or rolled back onto third fixation elements 172 to hold support member 120 in the folded position, while first fixation elements 170 remain available to attach to tissue.

Figure 3C:
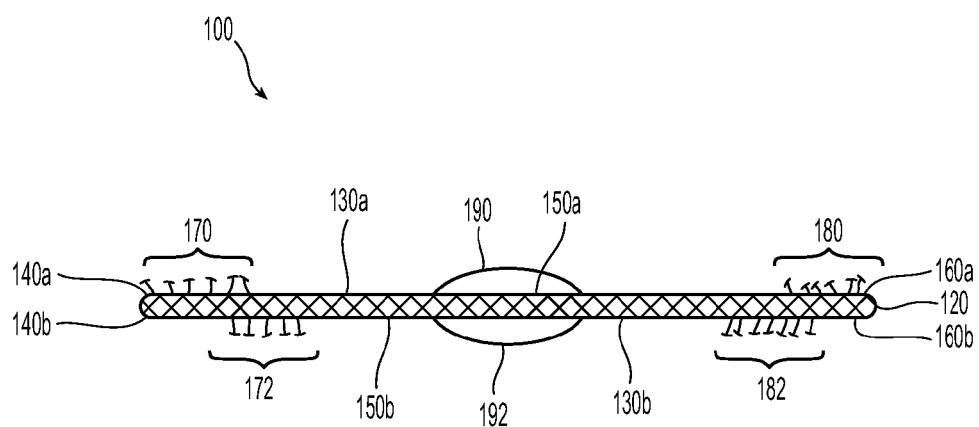

In some embodiments, as depicted in FIG. 3C, the implantable sling 100 further includes a second spacer 192 positioned on the central region 150b of the second surface 130b.

Figure 4A:
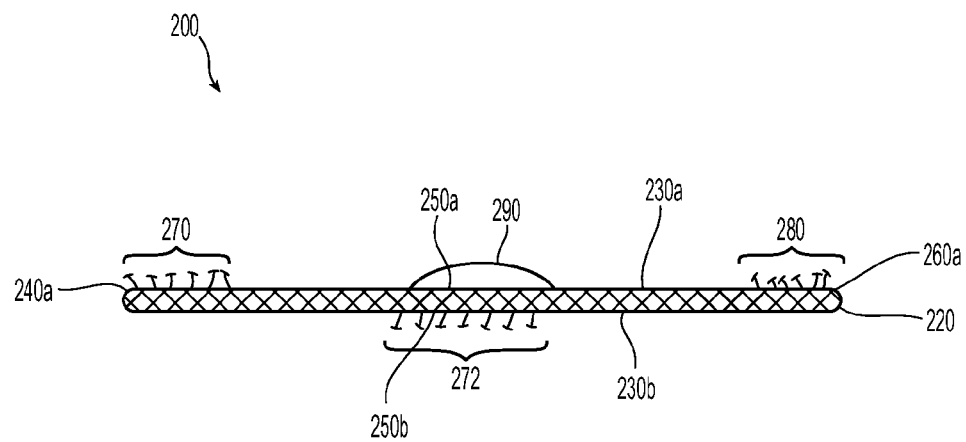
FIGS. 4A-4B are each a side view of a surgical sling in accordance with at least one embodiment described herein.
Figure 4B:
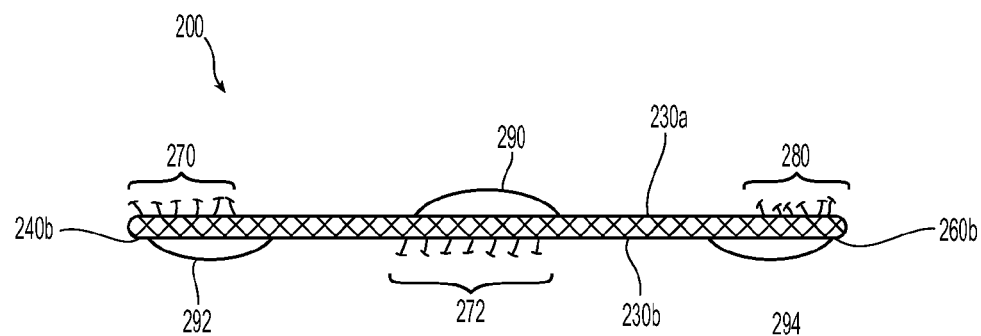

Referring to FIGS. 4A-4B, in some embodiments, the implantable sling 200 may include support member 220 including first surface 230a and a second surface 230b. The first surface 230a containing a first end 240a having a first set of fixation elements 270, a second end 260a having a second set of fixation elements 280, and a central region 250a including a first spacer 290. The second surface 230b containing a third set of fixation elements 272 positioned on the central region 250b opposite the first spacer 290.

As further illustrated in FIG. 4B, the implantable sling may further include a second spacer 292 positioned on the first end 240b of the second surface 230b and opposite the first set of fixation elements 270. A third spacer 294 may also be positioned on the second end 260b of the second surface 230b opposite the second set of fixation elements 280.

Figure 5:
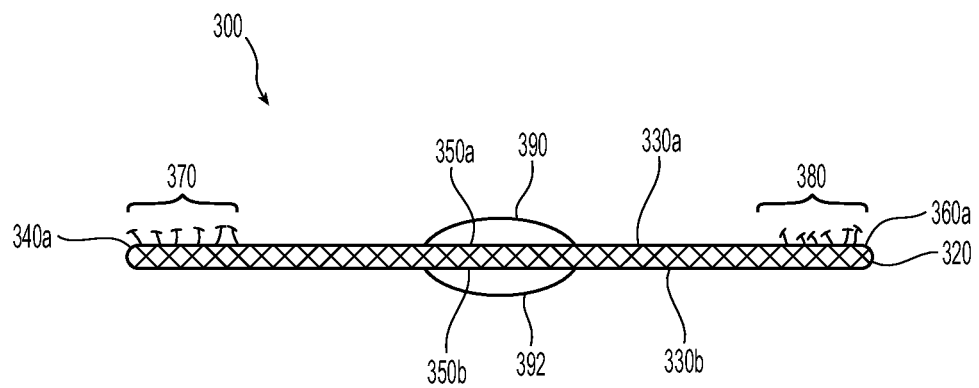
FIG. 5 is a side view of a surgical sling in accordance with at least one embodiment described herein.

Turning to FIG. 5, the implantable sling 300 may include in some embodiments, support member 320 including first surface 330a and a second surface 330b. The first surface 330a containing a first end 340a having a first set of fixation elements 370, a second end 360a having a second set of fixation elements 380, and a central region 350a including a first spacer 390. The second surface 330b containing including a second spacer 392 positioned on the central region 350b opposite the first spacer 390. In some embodiments, the support member is positioned longitudinally between the first and second spacers.

Figure 6:
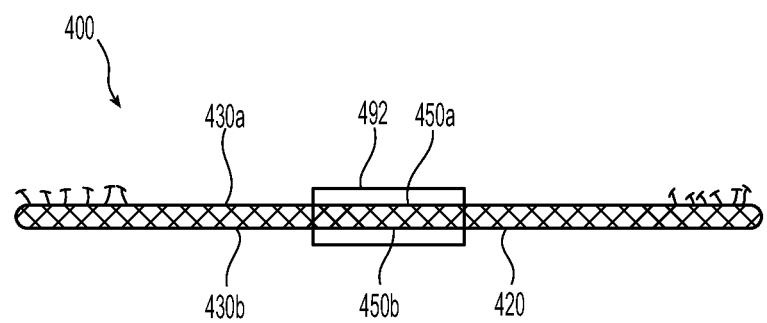
FIG. 6 is a side view of a surgical sling in accordance with at least one embodiment described herein.

In some embodiments, as illustrated in FIG. 6, the sling 400 may include a single spacer 492, which extends through the support member 420 and is positioned on the central regions 450a, 450b of both the first and second surfaces 430a, 430b.

Figure 7:
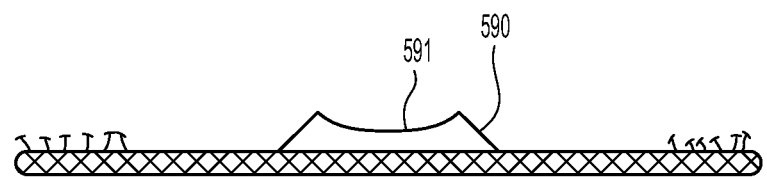
FIG. 7 is a side view of a surgical sling in accordance with at least one embodiment described herein.

In some embodiments, as depicted in FIG. 7, the spacer 590 may include a contoured top surface 591 to better accommodate the tissue the sling is intended to support. In this embodiment, the top surface 591 of the spacer 590 is concave to accommodate a tubular and/or rounded tissue surface. Of course, it is envisioned that the top surface of the spacer may be formed into any configuration suitable for accommodating the tissue, for example, the top surface of the spacer may be a convex surface.

As shown in FIGS. 8A-8B of the drawings, according to one embodiment, the implantable sling 600 is covered on the first and second surfaces 630a, 630b with a removable plastic sheath 640. As illustrated, the sheath 640 may include a top layer 641 and a bottom layer 642 which can be attached to each other to wrap around the implantable sling 600 to prevent interaction with the tissue prior to implantation. Although depicted as a two-piece removable sheath, it is envisioned that the sheath may include multiple pieces, as well as a single one-piece sheath.

The sheaths 640 may prevent the sling 600 from catching on the surrounding tissue during insertion and positioning of the sling 600 within the patient's body. Each sheath 640 preferably extends slightly beyond the width and length of the sling 600 to ensure that the sling 600 will not catch on the surrounding tissue during the surgical procedure. A sheath may also allow protection against contamination or damage.

The top layer 641 of sheath 640 may include a central cut-out 643 and at least one top perforation 646a, 646b which extends at least partially across the width of the top layer. In embodiments, the top perforation 646a, 646b extends from the cut-out 643 across the width of the top layer 641. The central cut-out 643 is intended to wrap-around the outer perimeter of the spacer 690. In this configuration, at least a portion of the spacer is not sealed within the sheath. Such a spacer may be positioned beneath the tissue in need of support prior to removal of the sheath without placing the sheath between the spacer and the tissue and preventing the sheath from being easily removed thereafter.

Bottom layer 642 may include a bottom perforation 648 which extends at least partially across the width of the bottom layer. The top and bottom perforations 646a, 646b, 648 are shown positioned near the midpoint, however, the top and bottom perforations may be positioned anywhere along the length of the top and bottom layer 641, 642. Although not shown, in embodiments, the bottom layer may also include at least one cut-out designed to accommodate any additional spacers positioned along the second surface of the sling.

In embodiments, the sheath and/or the sling may further include at least one line or marking to identify different portions of the implant. For example, as illustrated in FIGS. 1A, 1B, 8A and 8B, the plurality of lines may be equally spaced apart from each other and run across the width of the sling. In embodiments, the plurality of lines may be applied to the sheath. In embodiments, the sheath may be transparent so such lines may be visible to the surgeon prior to the removal of the sheath. In such embodiments, the surgeon may be able to determine the distance between the spacer and the tissue fixation elements needed to properly attach the implant to tissue.

According to various embodiments, when the sling is used to support the urethra, an exemplary procedure can comprise at least attaching a first end of the sling to an introducer, passing the introducer through a small vaginal incision beneath the urethra, rotating the introducer to insert the end of the sling including at least a first set of fixation elements into the obturator internus muscle, and releasing the first end from the introducer. Then the procedure is then repeated on the other side of the urethra so that second set of fixation elements positioned on the second end of the sling are deployed laterally to provide support to the sling while the spacer is located beneath the urethra. According to various embodiments, at least one of the first and second ends of the sling may be folded and/or rolled, either before or after the spacer is positioned beneath the urethra, to adjust the proper tension desired to provide tissue support. In embodiments, the spacer may be positioned beneath the urethra before the end(s) of the sling are folded and/or rolled, thereby applying the proper tension to the sling. No trimming of the sling is necessary. Thus no additional sharpened medical devices need to enter the site of implantation to trim the sling, which lessens the likelihood of piercing the surrounding tissue which is safer for the patient. The vaginal incision is then closed, and the procedure is complete.

According to various embodiments, each of the first and second set of fixation elements is placed laterally into each obturator internus muscle. The fixation elements do not penetrate deeply into this muscle and fascial lining, but rather attach superficially thereby inflicting little to no tissue damage. However, the fixation elements do attach, adhere and/or secure the sling in a position which can support tissue. The region around the obturator membrane has a well-defined anatomical structure, and provides a solid anchoring location for securing tissue anchors. This space is bordered by the inner bony rim of the obturator foramen.

According to various embodiments, the support members disclosed herein can be inserted via a single vaginal incision. In embodiments where the sling is secured in the respective obturator internus muscles, the sling does not need to exit through skin incisions (which is how the tension exerted by the sling on the urethra may be typically adjusted). Instead, the length of the sling can be altered by folding and/or rolling the ends to adjust the position and tension of the sling.

Figure 9:
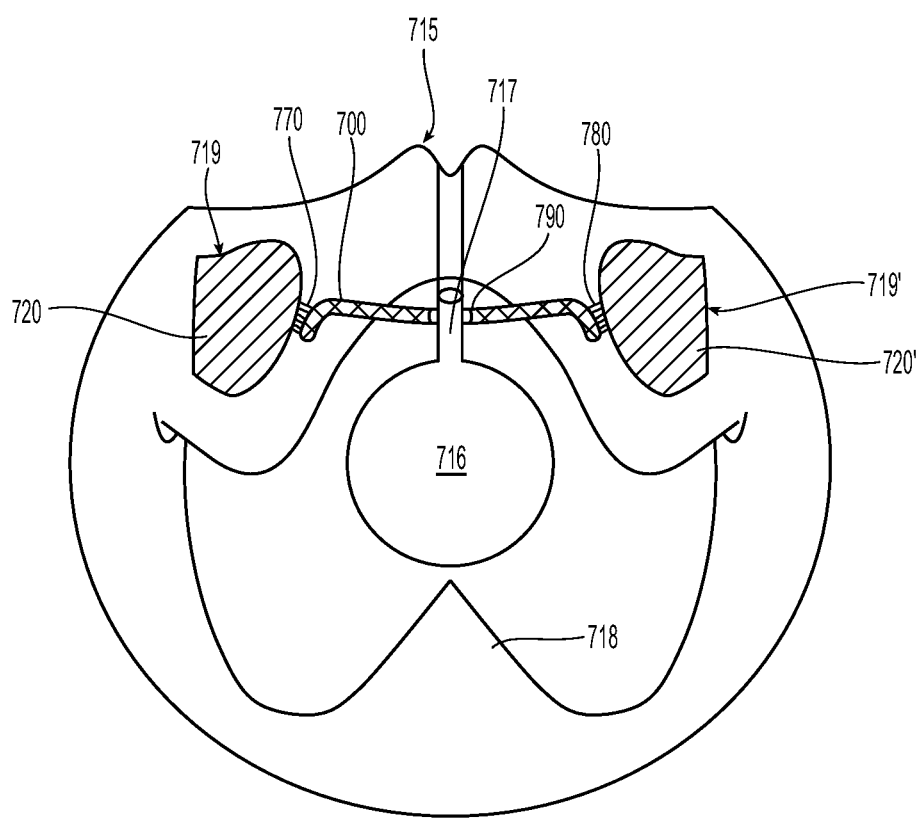
FIG. 9 illustrates an implanted sling in accordance with at least one embodiment described herein.

FIG. 9 illustrates an exemplary placement of a sling in accordance with various embodiments described herein. With a top-down view of the pelvis from behind, the pubic symphasis 715, bladder 716, urethra 717, sacrum 718, obturator foramina 719 and 719', and obturator internus muscle 720 and 720' can be seen. In accordance with various embodiments, the sling 700 is disposed beneath the urethra 717, and first and second sets of fixation elements 770, 780 are secured in the obturator internus muscle. Spacer 790 is positioned beneath the urethra 717.

Figure 10:
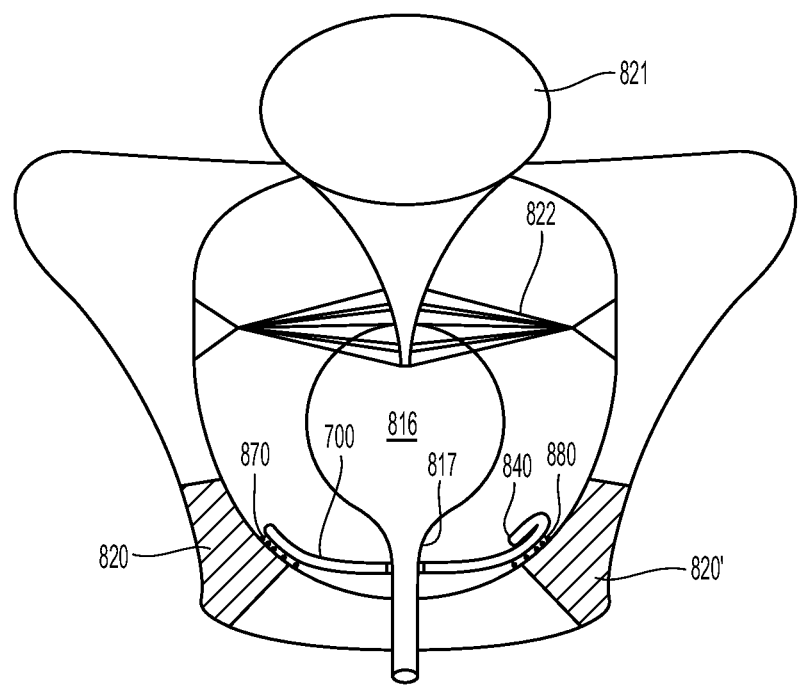
FIG. 10 illustrates an implanted sling in accordance with at least one embodiment described herein.

FIG. 10 illustrates a top-down view into the pelvis, including spine 821, and sacrospinous ligament 822. According to various embodiments, first and second sets of fixation elements 870, 880 are secured in the obturator internus muscle 820, 820'. As further illustrated, at least one end, i.e., the second end 840, is folded and/or rolled onto itself wherein a third set of fixation elements positioned on the second surface 830b of the sling 800 secures the sling 800 in this position and applies the proper tension to support the urethra 817.

Figure 11:
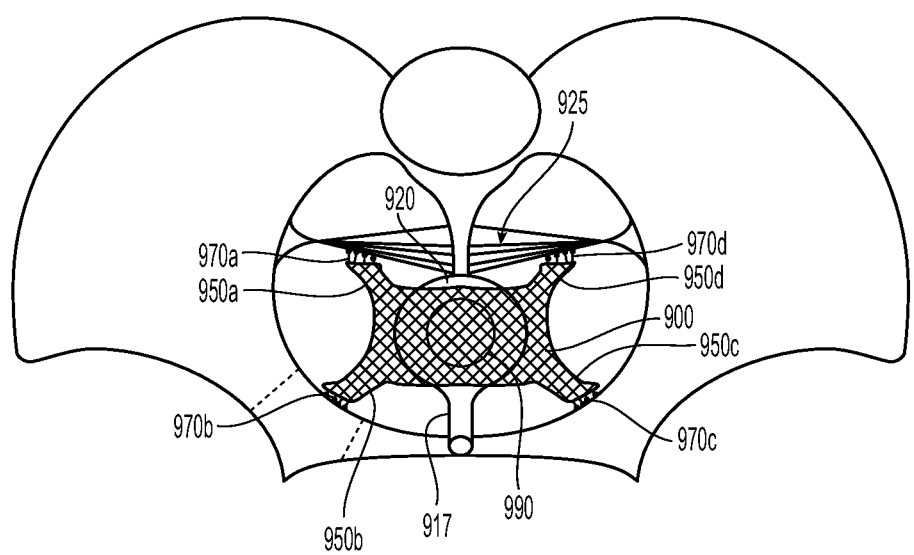
FIG. 11 illustrates a top-down view of a pelvis and a multi-arm sling supporting the bladder, in accordance with at least one embodiment described herein.

For applications other than a urethral sling, the support member may have a rectangular or other irregular shape to provide broader support to organs such as the bladder, rectum, bowel, etc. The support member may have multiple arms, with multiple sets of fixation elements providing multiple points of support around the perimeter of the support member. The support member may also be positioned at the vaginal apex, with the arms having anchors that are secured to the sacrospinous or uterosacral ligaments 925 to provide apical support to the vaginal vault. According to various embodiments, FIG. 11 illustrates the position of implant 900, which is used for pelvic floor repair, and includes multiple arms 950a-d including multiple sets of fixation elements 970a-d and at least one spacer 990. In some embodiments, the surface area of the spacer 990 may be smaller than the tissue being supported, i.e., the bladder 920. In other embodiments, the spacer may be of the same or larger size of the supported tissue.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how several forms of the implantable slings described herein may be embodied in practice.

What is claimed is:

1. A method of treating urinary stress incontinence comprising:

obtaining an implantable sling comprising a biocompatible support member having a first surface and a second surface, the first and second surfaces including a first end, a second end, and a central region positioned therebetween, a first set of fixation elements positioned on the first end of the first surface, a second set of fixation elements positioned on the second end of the first surface; a third set of fixation elements positioned on the second surface; and, a spacer positioned on the central region of the first surface, wherein the third set of fixation elements are positioned opposite the spacer;

positioning the spacer beneath a urethra;

attaching the first set of fixation elements to an obturator internus muscle on a first lateral side of the urethra and the second set of fixation elements to the obturator internus muscle on a second lateral side of the urethra.

2. The method of claim 1 wherein the implantable sling further comprises an outer sheath positioned around an outer perimeter of the implantable sling and including a central cut-out for exposing the spacer to allow direct contact with tissue prior to removal of the outer sheath; and removal of the outer sheath occurs after positioning of the spacer beneath the urethra.

3. The method of claim 1, wherein the biocompatible support member comprises a non-absorbable material.

4. The method of claim 1, wherein the biocompatible support member comprises an absorbable material.

5. The method of claim 1, wherein the biocompatible support member comprises a knit mesh.

6. The method of claim 1, wherein the biocompatible support member further comprises a second spacer positioned on the first end of the second surface opposite the first fixation elements.

7. The method of claim 6, wherein the biocompatible support member further comprises a third spacer positioned on the second end of the second surface opposite the second fixation elements.

8. The method of claim 7, wherein at least one of the spacer, the second spacer, or the third spacer comprises an absorbable material.

9. The method of claim 8, wherein at least one of the spacer, the second spacer, or the third spacer comprises a contoured surface designed to center tissue in need of support within the spacer.

10. The method of claim 1, further comprising a plurality of markings spaced equally apart from a center of the biocompatible support member.

11. An implantable sling for use in a medical application comprising:
    a biocompatible support member having a first surface and a second surface, the first and second surfaces including a first end, a second end, and a central region positioned therebetween;
    a first set of fixation elements positioned on the first end of the first surface;
    a second set of fixation elements positioned on the second end of the first surface;
    a third set of fixation elements positioned on the second surface; and,
    a spacer positioned on the central region of the first surface, wherein the third set of fixation elements are positioned opposite the spacer.

12. The implantable sling of claim 11, wherein the biocompatible support member comprises a non-absorbable material.

13. The implantable sling of claim 11, wherein the biocompatible support member comprises an absorbable material.

14. The implantable sling of claim 11, wherein the biocompatible support member comprises a knit mesh.

15. The implantable sling of claim 11, further comprising a second spacer positioned on the first end of the second surface opposite the first fixation elements.

16. The implantable sling of claim 15, further comprising a third spacer positioned on the second end of the second surface opposite the second fixation elements.

17. The implantable sling of claim 16, wherein at least one of the spacer, the second spacer, or the third spacer comprises an absorbable material.

18. The implantable sling of claim 16, wherein at least one of the spacer, the second spacer, or the third spacer comprises a contoured surface designed to center tissue in need of support within the spacer.

19. The implantable sling of claim 11, further comprising a plurality of markings spaced equally apart from a center of the biocompatible support member.

20. The implantable sling of claim 11, further comprising an outer sheath positioned around an outer perimeter of the sling.

21. The implantable sling of claim 20, wherein the outer sheath further comprises a central cut-out for exposing the spacer to allow direct contact with tissue prior to removal of the outer sheath.

* * * * *